United States Patent
Hanrahan et al.

(10) Patent No.: US 10,639,447 B2
(45) Date of Patent: May 5, 2020

(54) SYSTEM AND METHOD FOR MONITORING ANESTHETIC AGENT FILL LEVEL

(71) Applicant: General Electric Company, Schenectady, NY (US)

(72) Inventors: James Hanrahan, Madison, WI (US); Antti Tanner, Beijing (CN)

(73) Assignee: General Electric Company, Schenectady, NY (US)

( * ) Notice: Subject to any disclaimer, the term of this patent is extended or adjusted under 35 U.S.C. 154(b) by 273 days.

(21) Appl. No.: 15/819,361

(22) Filed: Nov. 21, 2017

(65) Prior Publication Data

US 2019/0151599 A1   May 23, 2019

(51) Int. Cl.
 *A61M 16/18*   (2006.01)
 *A61M 16/00*   (2006.01)

(52) U.S. Cl.
 CPC ........ *A61M 16/18* (2013.01); *A61M 16/0003* (2014.02); *A61M 2205/3306* (2013.01); *A61M 2205/3389* (2013.01); *A61M 2205/502* (2013.01); *A61M 2205/6063* (2013.01)

(58) Field of Classification Search
 CPC .............. A61M 16/18; A61M 16/0003; A61M 2205/3306; A61M 2205/3389
 See application file for complete search history.

(56) References Cited

U.S. PATENT DOCUMENTS

| | | | |
|---|---|---|---|
| 8,867,031 B2 | 10/2014 | Jones et al. | |
| 9,217,658 B2 | 12/2015 | Kuehl et al. | |
| 2012/0318263 A1 | 12/2012 | Jones et al. | |
| 2012/0318264 A1 | 12/2012 | Jones et al. | |
| 2015/0250961 A1* | 9/2015 | Whitman | A61M 16/0051 600/411 |
| 2016/0325055 A1* | 11/2016 | Cameron | A61M 11/005 |
| 2016/0331037 A1* | 11/2016 | Cameron | H04L 67/12 |
| 2019/0158938 A1* | 5/2019 | Bowen | H04W 4/20 |
| 2019/0344032 A1* | 11/2019 | McCormick | A61M 16/125 |

FOREIGN PATENT DOCUMENTS

EP    2645070    10/2013

* cited by examiner

*Primary Examiner* — Jamel E Williams
(74) *Attorney, Agent, or Firm* — Andrus Intellectual Property Law, LLP

(57) ABSTRACT

A system for monitoring anesthetic agents fill level in a vaporizer reservoir includes a camera configured to capture an image containing a sight glass on the vapor reservoir, just like, a processor, and an agent level module. The agent level module is executable to locate a sight glass portion within the image, an agent level edge within the sight glass portion, and minimum and maximum reference points within the image. A fill percentage is calculated based on a position of the agent level edge relative to the minimum and maximum reference points, and the remaining agent information is calculated based on the fill percentage and the known volume of the vaporizer reservoir.

20 Claims, 7 Drawing Sheets

SYSTEM AND METHOD FOR MONITORING ANESTHETIC AGENT FILL LEVEL

BACKGROUND

The present disclosure generally relates to systems and methods of monitoring the amount of anesthetic agent in a vaporizer reservoir, and more specifically to methods and systems of monitoring anesthetic agent fill level that do not require modification of, or installation on the anesthesia machine or anesthesia delivery system.

An anesthesia system may be implemented to deliver a predetermined dosage of anesthetic agent to a patient. The anesthesia system may be pneumatically connected to a vaporizer. Conventional vaporizers comprise a sump adapted to retain a liquid anesthetic agent, and a vaporization chamber adapted to convert the liquid anesthetic agent into a gas. The gaseous anesthetic agent is inhaled into the patient's lungs to produce an effect such as pain management, unconsciousness, preventing memory formation, and/or paralysis.

An anesthesiologist monitors the level of anesthetic agent in the vaporizer to ensure sufficient anesthetic agent is available for treatment of a patient. The level of the anesthetic agent may be viewed through a glass tube or transparent portion of the vaporizer, referred to as a sight glass. As the anesthetic agent is vaporized, the liquid level of the anesthetic agent can be seen visually to fall in the sight glass, providing a visual indication of the level of anesthetic agent remaining in the vaporizer.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for monitoring anesthetic agents fill level in a vaporizer reservoir includes a camera configured to capture an image containing a sight glass on the vapor reservoir, just like, a processor, and an agent level module. The agent level module is executable to locate a sight glass portion within the image, an agent level edge within the sight glass portion, and minimum and maximum reference points within the image. A fill percentage is calculated based on a position of the agent level edge relative to the minimum and maximum reference points, and the remaining agent information is calculated based on the fill percentage and the known volume of the vaporizer reservoir.

In one embodiment, a method for monitoring anesthetic agent fill level in a vaporizer reservoir includes receiving an image of a vaporizer reservoir, the vaporizer reservoir having a known volume for containing liquid anesthetic agent. Using machine vision software, the method includes locating a sight glass portion, minimum and maximum reference points, and an agent level edge within the image. A fill percentage is calculated based on a position of the agent level edge relative to the minimum and maximum reference points. The remaining agent information has been calculated based on the fill percentage, and the remaining agent information is displayed.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their experimentation and research in the relevant field, the present inventors have recognized a need for a system and method of monitoring anesthetic agent fill level that can be used on any existing vaporizer system without having to modify the vaporizer system. Further, the inventors have recognized a need for such systems and methods that are capable of determining a consumed volume of anesthetic agent over time. In view of the needs and problems recognized in the field, the inventors developed the disclosed system that utilizes a camera configured to capture an image of the vaporizer reservoir, and specifically including the sight glass on the vaporizer reservoir. The system uses machine vision software to automatically detect the agent level edge within the sight glass and determine remaining agent information, such as an amount of anesthetic agent remaining in the vaporizer reservoir and a remaining therapy time given that remaining agent amount. The system may also be configured to capture multiple images of the vaporizer reservoir throughout a therapy session in order to track the amount of agent in the vaporizer reservoir and calculate a consumed volume of anesthetic agent over a period of time, such as a total amount of agent delivered to a patient during a medical procedure.

Figure 1:
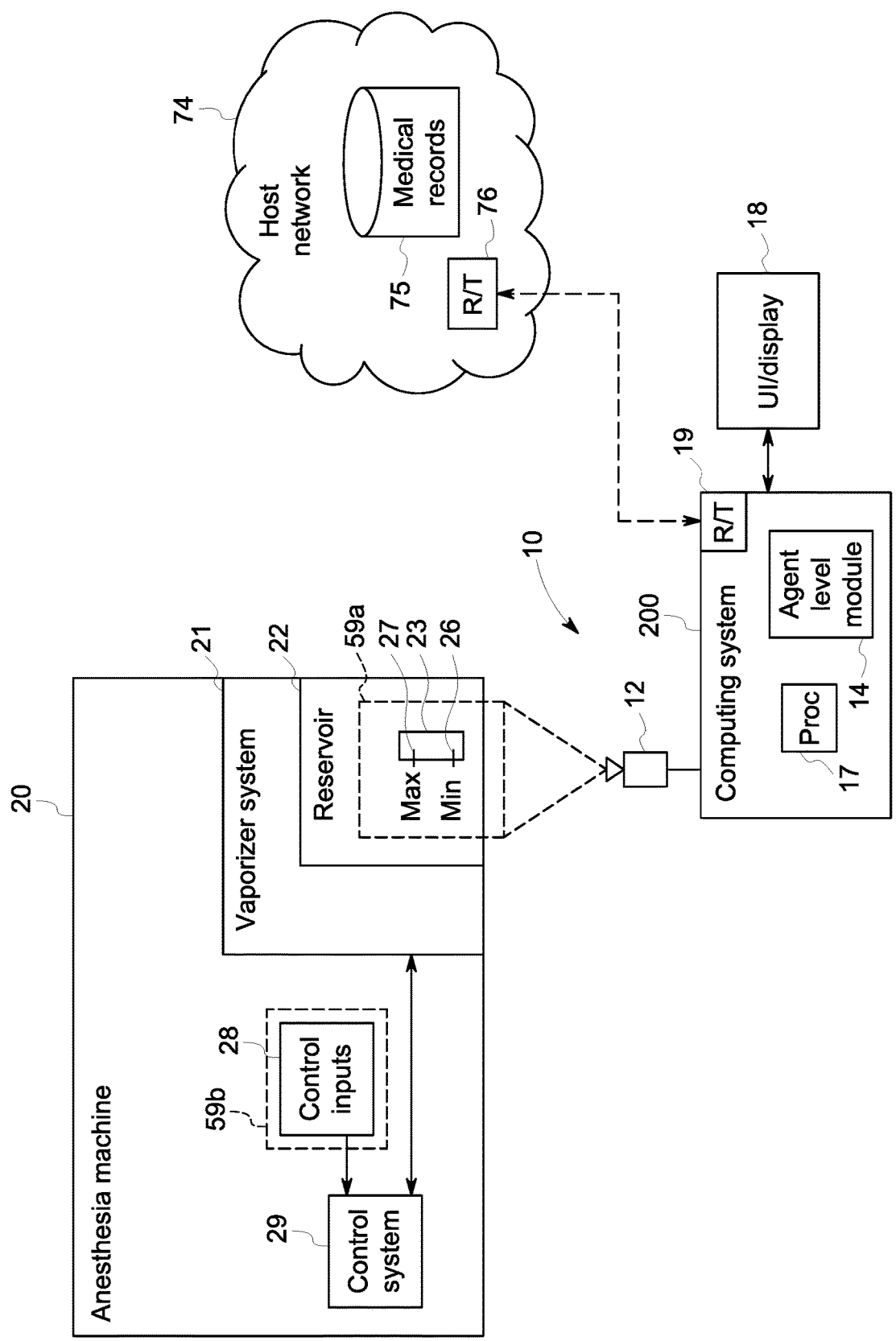
FIG. 1 is a schematic representation of a system for monitoring anesthetic agent fill level in a vaporizer reservoir of an anesthesia delivery system.

FIG. 1 schematically depicts one embodiment of a system 10 for monitoring anesthetic agent fill level in a vaporizer reservoir 22. The system 10 includes at least one camera 12 configured to capture an image of the vaporizer reservoir 22, and specifically an image containing the sight glass 23 of the vaporizer reservoir 22. The camera 12 may be arranged and configured to image all or a portion of the vaporizer reservoir 22, exemplified in FIG. 1 as imaged area 59a, and/or other portions of the anesthesia machine 20 (such as the control inputs as represented as imaged area 59b). The images captured by the camera 12 are provided to the computing system 200. The computing system 200 includes an agent level module 14 that processes the images in order to calculate remaining agent information, such as remaining agent amount 66 and remaining therapy time 68 (see FIG. 3). The agent level module 14 may further be configured to receive multiple images 30 (see FIG. 2) containing the sight glass taken over time, and to calculate a consumed volume 70 of anesthetic agent over time. The agent level module 14 may further be configured to automatically detect the type of anesthetic agent in the reservoir 22 and/or to determine control settings for the vaporizer system 21, such as the fresh gas flow rate and/or the vaporizer concentration. Alternatively or additionally, the agent level module 14 may further be configured to generate one or more agent information images 45 on a display of a user interface 18. The agent level module 14 is a set of software instructions executable on a processor 17 of the computing system 200.

Accordingly, the system 10 monitors anesthetic agent fill level in any type of vaporizer reservoir 22 having a sight glass 23 without requiring modification of, or integration into, the reservoir 22 or vaporizer system 21. The anesthesia machine 20 is generally configured to deliver anesthesia to the patient, including anesthetic gas comprised of a mixture of fresh gases and anesthetic gases. For example, the gas may include oxygen ($O_2$) provided from an oxygen tank, nitrous oxide ($N_2O$) provided by an $N_2O$ tank, and a vaporized anesthetic agent, such as Sevoflurane, Desflurane, Isoflurane, Enflurane, etc. The anesthetic agent is vaporized by a vaporizer system 21. The anesthetic agent is contained in liquid form in a vaporizer reservoir 22, which includes a sump adapted to retain the liquid anesthetic agent.

The vaporizer system 21 converts the liquid anesthetic agent contained in the vaporizer reservoir 22 into a vaporized anesthetic agent. More specifically, the vaporizer system 21 introduces the vaporized anesthetic agent into the pneumatic circuit provided by the anesthesia machine 20. The anesthesia machine generally includes control inputs 28 for the vaporizer system 21, such as to allow a clinician to control the fresh gas flow rate (e.g. $O_2$ and/or $N_2O$) and vaporizer concentration. For example, the control inputs may be digital, such as control inputs provided via a touch screen presenting a digital user interface, or analog such as control dials movable to a certain position in order to provide an input value. The control values from the control inputs 28 are provided to the control system 29 for the anesthesia machine 20, which then controls the vaporizer system 21, including disbursement of liquid anesthetic agent from the vaporizer reservoir 22 to the patient.

The level of liquid anesthetic agent in the vaporizer reservoir 22 is viewed through the sight glass 23, which is generally viewed by an operating clinician anesthesiologist. The liquid anesthetic agent contained in the reservoir 22 decreases as the agent is vaporized and delivered to the patient, and thus the agent level edge seen through the sight glass moves downward accordingly. Level markers are typically associated with the sight glass 23 such as a maximum fill line 27 and a minimum fill line 26. The maximum and minimum fill lines 27, 26 provide comparative markers by which the fill level is approximated. Generally, the clinician watches to see when the agent level edge reaches the minimum fill line, at which time the vaporizer reservoir 22 is refilled with liquid anesthetic agent.

The inventors have recognized that most vaporizer systems 21 and anesthesia machines 20 do not provide detailed information regarding volume of remaining anesthetic agent or remaining therapy time, and do not provide any easy and accurate way of obtaining and/or tracking such information. Accordingly, the disclosed system 10 was developed which images the sight glass 23, locates the agent level edge 34, and precisely calculates a fill percentage based thereon. Specifically, the agent level module 14 processes the image to locate a minimum reference point and a maximum reference point within the image, which may be within a sight glass portion of the image or outside of that, such as a bottom and top of the vaporizer reservoir 22, or the like. To provide one example, the minimum and maximum reference points may be the minimum fill line 26 and the maximum fill line 27 associated with the sight glass 23. As another example, the minimum reference point and maximum reference point may be the bottom and top edges of the sight glass 23, such as the edges where the translucent portion of the sight glass meets the housing of the vaporizer reservoir 22.

Figure 2:
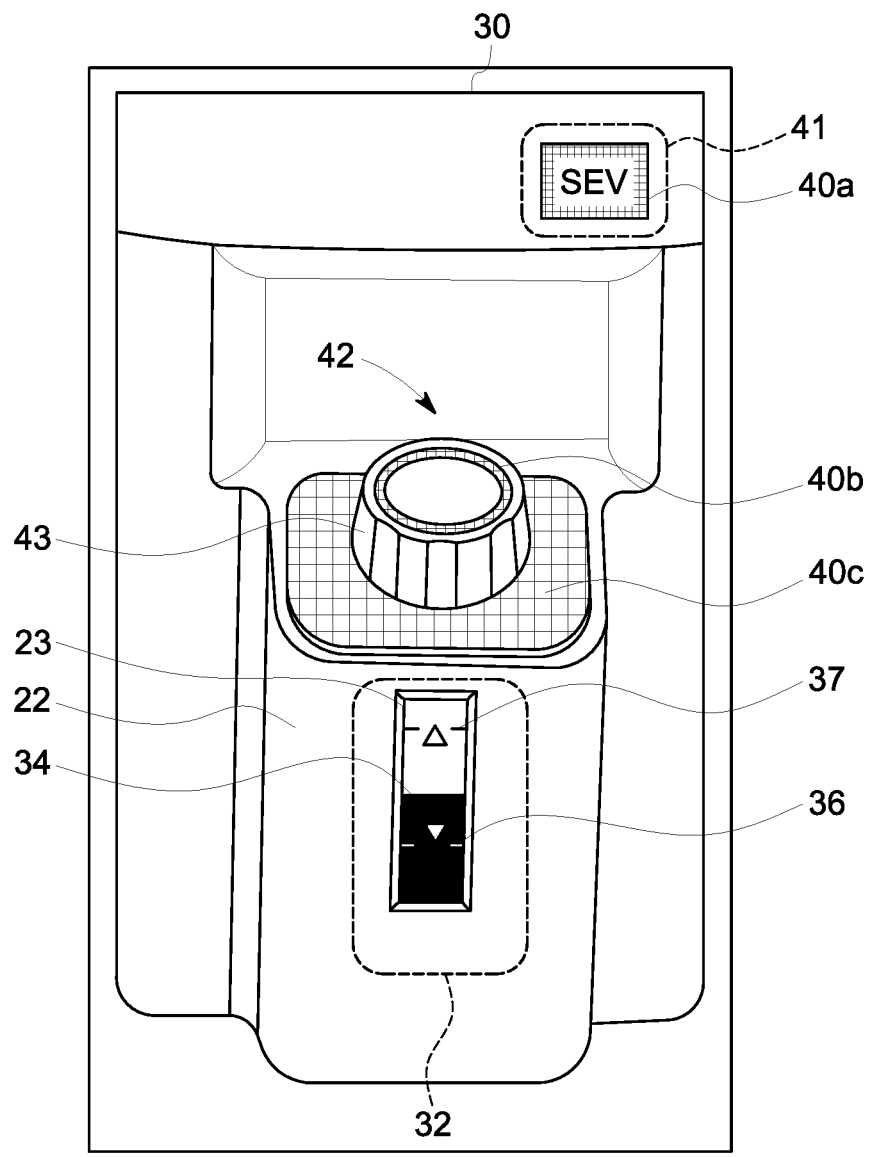
FIG. 2 depicts an example of an image containing a sight glass generated and utilized by the disclosed system for monitoring anesthetic agent fill level.

FIG. 2 depicts one embodiment of an image 30 containing a sight glass 23 of the vaporizer reservoir 22. The image 30 is captured by the camera 12 and processed by the agent level module 14 as disclosed herein. The agent level module 14 contains executable instructions to first locate a sight glass portion 32 within the image 30. Specifically, the agent level module contains machine vision software that locates the portion of the image 30 that captures the sight glass 23 on the vaporizer reservoir 22, such as via feature and pattern recognition within the image data.

The agent level module 14 locates an agent level edge 34 within the sight glass portion 32 of the image 30. A minimum reference point 36 and a maximum reference point 37 are also recognized within the image, which as described above may reside within the sight glass portion 32. The agent level module 14 then compares the position of the agent level edge 34 to the minimum reference point 36 and/or the maximum reference point 37 in order to calculate a fill percentage. For example, the agent level module 14 may compare the position of the agent level edge 34 to one of the minimum reference point 36 and the maximum reference point 37 and a calculated distance between the located minimum and maximum reference points 36, 37. Namely, the agent level module 14 measures the agent level edge 34 with respect to two fixed and known reference points.

Figure 3:
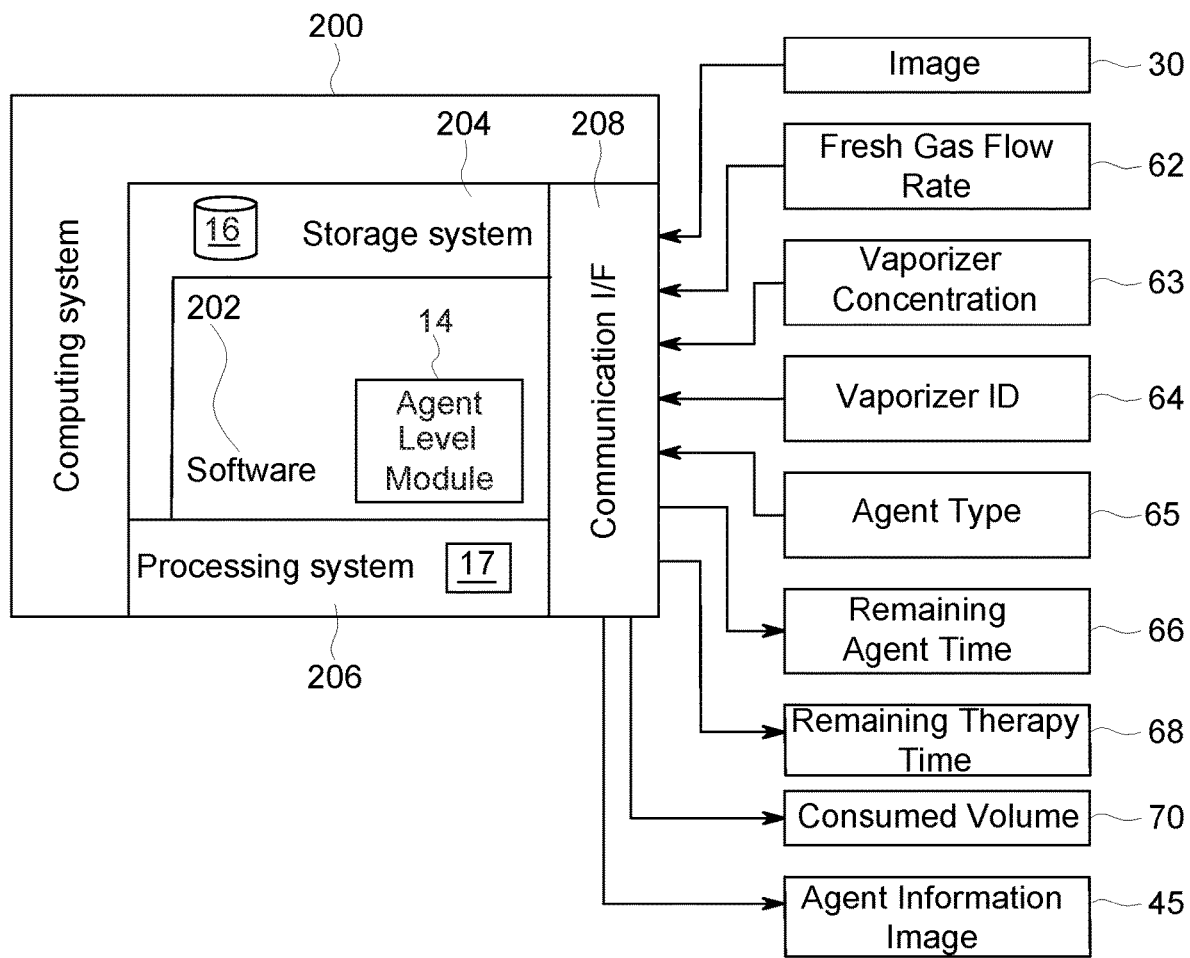
FIG. 3 is a schematic representation of a computing system portion of a system for monitoring anesthetic agent fill level of the present disclosure.
Figure 4:
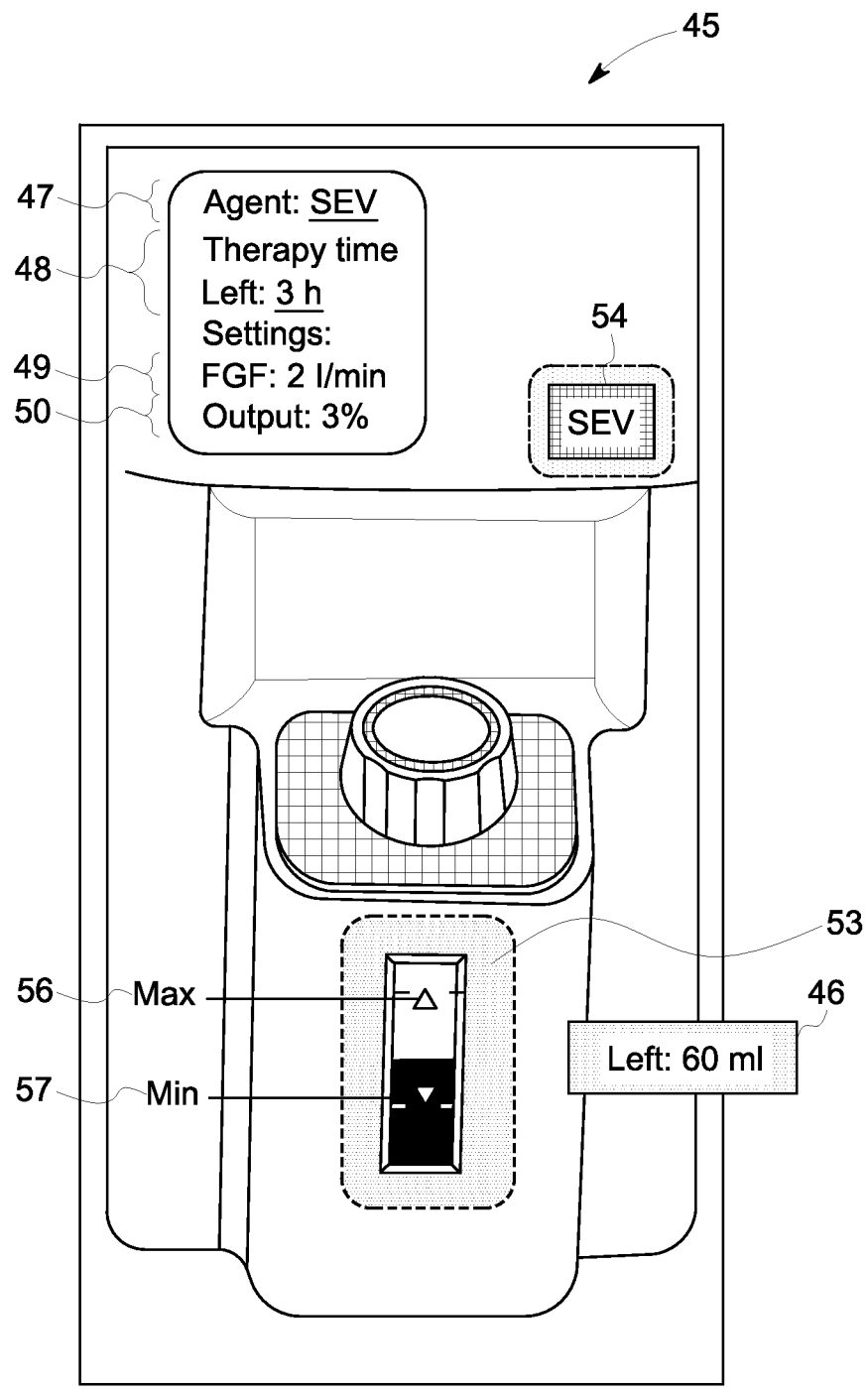
FIG. 4 provides one example of an agent information image generated by the disclosed system for monitoring anesthetic agent fill level.

As also illustrated with respect to FIGS. 3 and 4, the agent level module accesses a known volume for the vaporizer reservoir 22. For example, the agent level module 14 may access a lookup table or database containing reservoir volumes, such as based on a brand and model number for a vaporizer system 21 and/or based on an agent type. For example, the computing system 200 may store a lookup table containing known volumes based on the vaporizer system identification 64. The agent level module 14 then calculates remaining agent information, such as remaining agent amount 66 and remaining therapy time 68, based on the fill percentage and the known volume of the vaporizer reservoir 22. The remaining agent information can then be provided to the clinician, such as on the display of the user interface 18.

In certain embodiments, information about the anesthesia machine 20 and vaporizer system 21 may be provided by the operator such as via the user interface 18. For example, the user may enter a vaporizer identification 64, such as a make and model of the vaporizer system 21. The operator may also enter an agent type 65, which is the type of anesthetic agent contained in the reservoir 22 being imaged. In certain embodiments, the operator may also provide a fresh gas flow rate 62, which is the rate at which the carrier gas into which the anesthetic is being vaporized is flowing. The operator may also input a vaporizer concentration 63 which is the concentration of the anesthetic agent in the gas delivered to the patient. In certain embodiments, the operator may also input the type of fresh gas, also referred to as carrier gas. The most common type of carrier gas is air. In certain examples, the agent level module 14 may be configured to generate a prompt on the user interface display 18 instructing an operator to enter one or more of the vaporizer identification, the agent type, the current fresh gas flow rate, and/or the current vaporizer concentration setting.

Alternatively, the agent level module 14 may be configured to automatically recognize the vaporizer system, the agent type, or control settings for the vaporizer system 21. Exemplary methods for doing so are described herein below. In embodiments where the vaporizer type and/or agent type are not identified based on user input, the agent level module 14 may automatically determine that information based on the captured image(s) 30. For example, the agent level module 14 may locate an agent label 40 within the image 30 that denotes the anesthetic agent type contained in the vaporizer reservoir 22.

The agent label 40 may take any of various forms, such as alphanumeric labeling or color coding. In the depicted example, the agent label 40 contains both alphanumeric and color coding labels. Agent labels generally conform to standards, such as using a standardized color coding system and set of letters for each agent type. In the depicted embodiment at FIG. 2 the agent label 40 includes multiple different agent labels 40a, 40b, 40c. All three agent labels are depicted in yellow, which is the standard color coding for Sevoflurane. The agent label 40a also includes the letters SEV, which is the standard alphanumeric code for Sevoflurane.

In certain embodiments, the agent level module 14 may identify an agent label portion 41 within the image, and conduct character recognition to detect the alphanumeric agent label. In other embodiments, the agent level module 14 may conduct character recognition of the entire image to detect any words therein, and then determine if the agent label is provided therein. Alternatively or additionally, the agent level module 14 may assess whether one of a set of predefined standard color indicators is present, such as by detecting areas containing at least a predetermined amount of one of the standard color indicators. Furthermore, the agent level module 14 may look for one of the standard color indicators based on particular reference points, which may also be identified by the image processing software. For example, the image processing software may locate the boundaries of the vaporizer reservoir 22, as well as features thereon, such as the fill port 42 of the vaporizer reservoir 22 and/or the cap 43 covering the fill port.

Agent labels tend to be in certain standard locations on certain vaporizer systems 21, and thus the agent level module 14 may be configured to assess areas of the image based on location of already-identified and/or key reference points, such as the sight glass portion 32, the fill port 42, the cap 43, etc. For example, agent labels are often provided on or adjacent to the fill port 42 and/or cap 43. In the depicted embodiment, the agent label 40C is a color indicator block surrounding the fill port 42, and agent label 40b is a circular ring color indicator on the cap 43. In another embodiment, the agent level module 14 may be configured to detect one of a predefined set of color indicators forming a predefined shape or pattern that is standard for agent labels, such as the circular ring color indicator 40b on the cap 43, or the square agent label 40a.

The vaporizer system may be identified based on certain patterns within the image that indicate, or are particular to, a particular vaporizer system. For example, each vaporizer system type has a uniquely designed exterior appearance or housing of the vaporizer reservoir 22, and thus the make and model of the vaporizer system 21 may be identified based on the shape, color, and contour of the vaporizer reservoir 22. This includes the overall shape of the vaporizer reservoir, the shape, location, and look of the sight glass 23, the location of the fill port 42, the shape and look of the cap 43, the placement of the agent label(s) 40, and the like. Alternatively or additionally, the agent level module 14 may look for an alphanumeric label of the vaporizer system, such as a trademark or model label within the image.

In certain embodiments, the agent level module 14 may be configured to automatically recognize the control inputs 28, such as the fresh gas flow rate value and/or the vaporizer concentration. For example, the agent level module 14 may be configured to recognize the control inputs 28 within an input image 30, and determine the values based on the position of the input dials, for example. In other embodiments, the agent level module 14 may communicate with a control system 29 of the anesthesia machine and may receive certain information therefrom, such as the fresh gas flow rate 62, vaporizer concentration 63, vaporizer identification 64, agent type 65, and the like. For example, the computing system 200 may include a receiver transmitter that communicates with a receiver transmitter on the anesthesia machine 20. For example, the receiver/transmitter 19 of FIG. 1 may communicate with a receiver transmitter (not shown) on the anesthesia machine to communicate signals to the control system 29 and/or receive wireless communication data from the control system 29. Such wireless communication may be provided according to any wireless means, including any wireless protocol utilized for secure transfer of mathematical and patient information.

Once the agent type, fresh gas flow 8, and vaporizer concentration are known, a remaining therapy time 68 can be calculated, which is the amount of time at which the current vaporizer concentration can be maintained given the fresh gas flow rate, agent type, and remaining agent amount. Accordingly, the remaining therapy time 68 instructs an operator, such as a clinician or anesthesiologist, on how much time they have at the current delivery values before the vaporizer reservoir 22 will need to be refilled.

In certain embodiments, the camera 12 may be operated to produce multiple images 30 containing the sight glass 23, where the multiple images 30 are taken over time in order to track the fill level in the vaporizer reservoir 22. For example, a first image may be taken at the beginning of anesthesia delivery during a procedure, and a second image may be taken at the end of the anesthesia delivery for the procedure. A first remaining agent amount is determined based on the first image, such as indicating the amount of anesthetic agent in the vaporizer reservoir 22 at the start of anesthesia delivery. A second remaining agent amount may be calculated after or at the conclusion of the anesthesia delivery, indicating the amount of anesthetic agent remaining in the vaporizer reservoir 22 after conclusion of the anesthesia delivery period. The difference between the first remaining agent amount and the second remaining agent amount indicates a consumed volume 70 of anesthetic agent during the anesthetic delivery period. In certain embodiments, additional images may be taken throughout the anesthetic delivery period. For example, images may be taken periodically in order to track anesthesia delivery. Furthermore, images may be taken prior to and after refill of the vaporizer reservoir 22 with liquid anesthetic agent. The consumed volume 70 may be tracked with each new image taken during the anesthesia delivery period, for example.

The remaining agent amount 66, remaining therapy time 68, and consumed volume 70 are visually conveyed to the operator, such as via the user interface display 18. The display may be provided in any number of ways, such as a list, text output, or other visual display of the remaining agent information. To provide just one example, the agent information may be provided in an agent information image 45, which may be overlaid onto a static image of the vaporizer reservoir or onto a video, or dynamic image of the vaporizer reservoir, such as in a virtual reality fashion. FIG. 4 depicts one example of an agent information image 45 overlaid onto an image 30 containing the sight glass, which may be a single static image or a continuous set of images provided as a video. In FIG. 4, the agent information image 45 contains a remaining agent amount indicator 46 indicating the remaining agent amount 66 calculated by the agent level module 14. Similarly, the agent information image 45 contains a minimum line indicator 56 and a maximum line indicator 57 indicating the identified locations within the image of the minimum reference point 36 and the maximum reference point 37 on the vaporizer reservoir 22. In other embodiments where the minimum reference point and the maximum reference point are at other locations, the minimum line indicator 56 and the maximum line indicator 57 may be provided at those locations as opposed to in correspondence with the minimum and maximum fill lines 26, 27.

The agent information image 45 further provides an agent indicator 47 indicating the agent type 65, a remaining therapy time indicator 48 indicating the calculated remaining therapy time 68, a fresh gas flow rate indicator 49, and a vaporizer concentration 50. In certain embodiments, the agent information image 45 may further provide a sight glass portion indicator 53 indicating the identified sight glass portion 33 within the image 30 and an agent level portion indicator 54 demarcating the agent label portion 41 within the image 30. This allows the operator to verify that the machine vision software of the agent level module 14 properly identified the sight glass portion 33 and the agent label portion 41. In other embodiments, the agent information image 45 may also provide a consumed volume 70.

In certain embodiments, the agent level module 14 may be configured to facilitate transmission of one or all of the determined values to a host network 74, such as the network for the hospital for healthcare facility, where the information can be stored in the patient's medical record 75. For example, the computing system 200 may comprise a receiver/transmitter 19 that communicates with a receiver transmitter 76 associated with the host network 74. The host network may comprise a computing system, or a network of computing systems, that facilitate transmission and storage of the relevant information into the patient's medical record 75. For example, one or more of the remaining agent amount 66, remaining therapy time 68, consumed volume 70, and/or agent information image 45 may be stored in the patient's medical record 75, along with a time stamp indicating the time at which such values were determined. Similarly, the agent level module 14 may transmit other information, in conjunction with the remaining agent information, such as the fresh gas flow rate 62, the vaporizer concentration 63, the vaporizer ID 64, the agent type 65, or the like. Such information may be communicated regardless of whether it was inputted by the operator, received from the control system 29, or determined by the agent level module 14, and such determination/receipt mechanism may also be indicated and stored.

In certain embodiments the system 10 for monitoring the anesthetic agent fill level may be contained in a portable computing device, such as a cell phone, tablet, or the like. In such an embodiment, the agent level module 14 may be an application executed on the portable computing device, such as on the processor 17 thereof. Similarly, the user interface display 18 may be that of a standard portable computing device, as with the camera 12, receiver/transmitter 19, and display 18. In other embodiments, the system 10 for monitoring anesthetic agent may be a dedicated device, which may be portable or permanently installed in association with an anesthesia machine 20. In such an embodiment, the computing system 200 may be configured to automatically control the camera 12 in order to capture the needed images, such as of the various imaged areas 59a, 59b. The agent level module 14 may, for example, send control signals to a control module for the camera 12 in order to move or adjust the lens focus. Alternatively, the agent level module 14 may digitally zoom or focus on portions of a wider angle image captured by the camera 12, such as of large sections or the entirety of the anesthesia machine 20. In embodiments where the system 10 is implemented utilizing a portable computing device, the agent level module 14 may provide instructions to an operator regarding where on the anesthesia machine 20 should be imaged—such as instructing a user to direct the camera 12 lens on a portion of the vaporizer reservoir 22 containing the sight glass 23, or on a portion of the anesthesia machine 20 containing the control inputs 28. Thereby, the needed images 30 can be captured and the appropriate information acquired therefrom.

FIG. 3 is a schematic diagram of the computing system 200, including the agent level module 14 that facilitates executions of the functions described herein. The computing system 200 includes a processing system 206, storage system 204, software 202, and a communication interface 208. The processing system 206 loads and executes software 202 from the storage system 204, including the agent level module 14. The agent level module 14 includes computer-readable instructions that, when executed, direct the processing system 206 to operate as described in herein in further detail.

Although the computing system 200 as depicted in FIG. 3 includes one software 202 encapsulating one agent level module 14, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 17, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which includes the database or lookup table 16 of known vaporizer reservoir volumes, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the lookup table 16. Likewise, the agent level module 14 can be stored, distributed, and/or implemented across one or more storage media or group of storage medias.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the camera 12, the receiver/transmitter 19, the user interface display 18 (or a controller therefor), and the control system 29 of the anesthesia machine 20.

Figure 5:
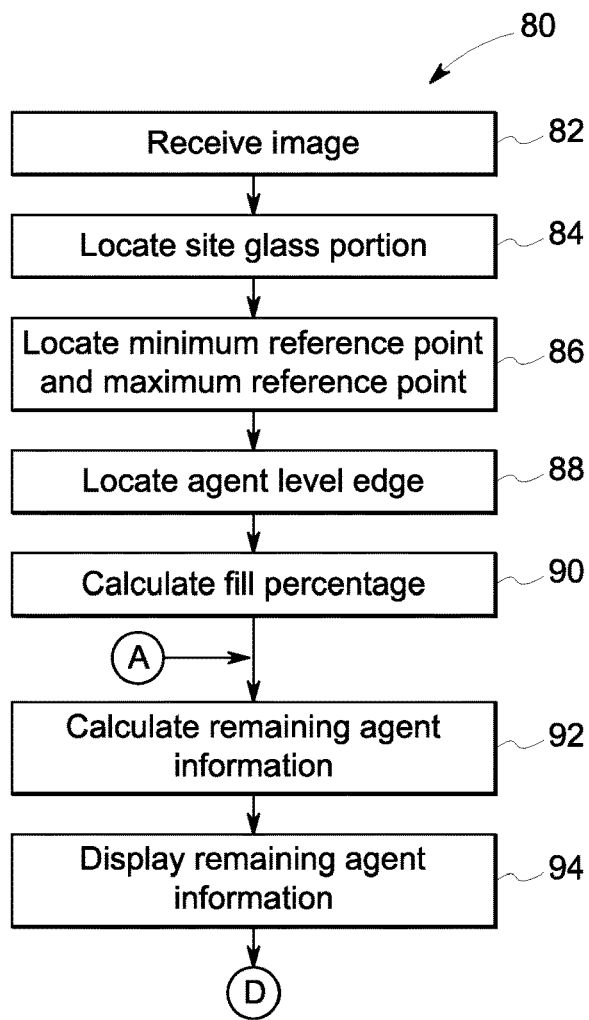
FIGS. 5-8 depict various embodiments of methods, or portions thereof, of monitoring anesthetic agent fill level in a vaporizer reservoir.

FIGS. 5-8 depict various embodiments of methods 80, or portions thereof, for monitoring anesthetic agent fill level. Referring to FIG. 5, an image 30 is received at step 82, and a sight glass portion 32 is located within the image 30 at step 84. A minimum reference point 36 and a maximum reference point 37 are also located within the image 30, represented as step 86. The agent level edge 34 is located within the image 30 at step 88. The fill percentage is calculated at step 90 by relating the agent level edge 34 to the minimum reference point 36 and the maximum reference point 37. In certain embodiments, this may be accomplished by comparing the position of the agent level edge 34 to one of the minimum reference point 36 and the maximum reference point 37 and a calculated distance between the located minimum and maximum reference points 36, 37. Remaining agent information is calculated at step 92, and then displayed at step 94. Additional steps may be executed within that method, such as at point A depicted in FIG. 5.

Figure 6:
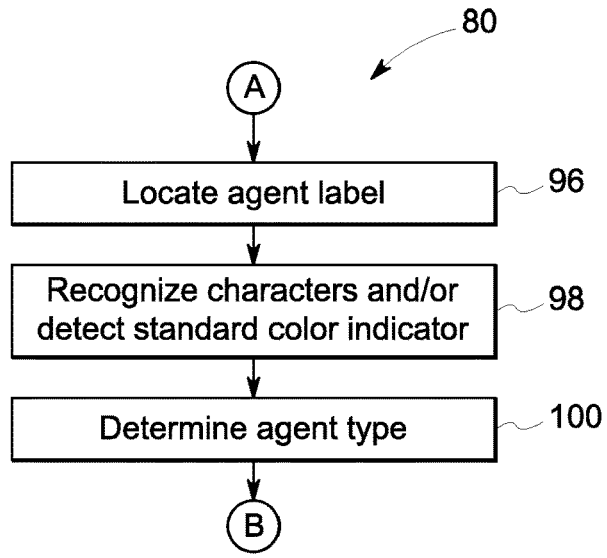

For example, after locating the agent level edge 34 and/or calculating the fill percentage, an agent label may be located within the image, represented at step 96 in FIG. 6. The agent level module 14 may include character recognition software and/or color recognition software in order to recognize standard characters and/or a standard color indicator for an agent type. After the characters and/or standard color indicator are recognized at step 98, an agent type is determined based thereon at step 100. As described above, the step in FIG. 6 may be avoided if an agent type 65 is received by the computing system 200 either via operator input or via communication from the control system 29 at the anesthesia machine 20.

Figure 7A:
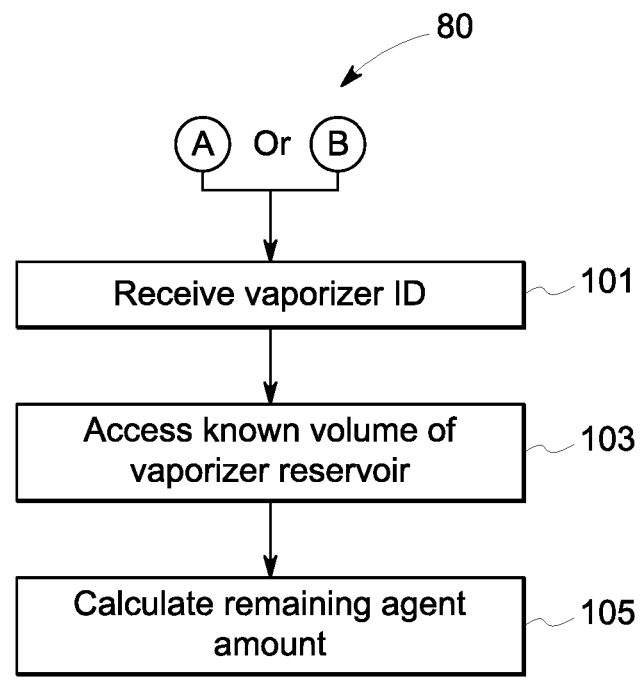

As depicted in FIG. 7A, a vaporizer ID is received at step 101, which may be automatically determined based on images received by the agent level module 14, received from operator input, or by communication from the control system 29. The vaporizer ID is used to access a known volume for the vaporizer reservoir 22 at step 103. For example, a lookup table may be available associating vaporizer ID with known volumes. The remaining agent amount is then calculated at step 105 based on the fill percentage determined at step 90 and the known volume of the vaporizer reservoir.

Figure 7B:
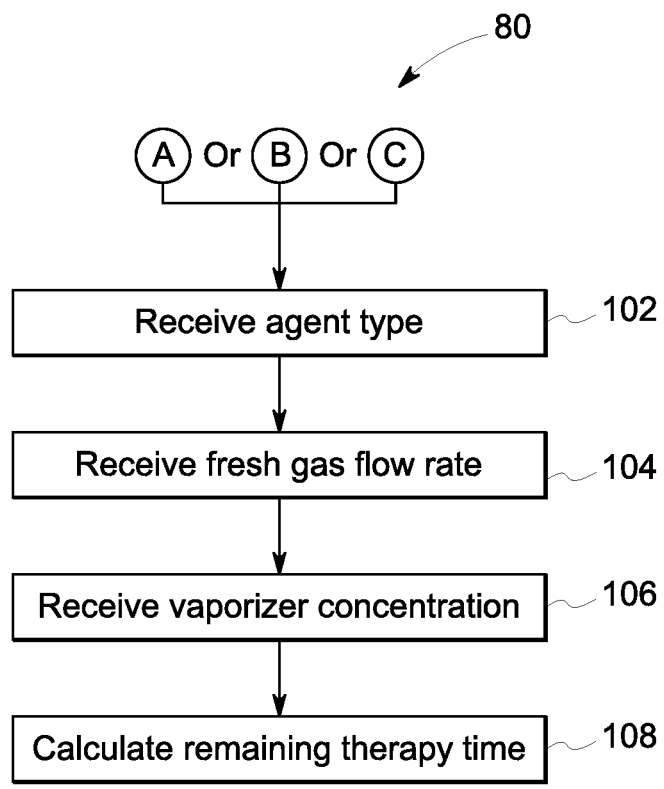

In certain embodiments, the steps at FIG. 7B may also be executed to determine the remaining therapy time. The agent type is received at step 102, such as after determination according to the steps in FIG. 6, or via communication from the operator through the user interface display 18 or by communication from the control system 29. The fresh gas flow rate is received at step 104 and the vaporizer concentration is received at step 106, which may be calculated and/or received similarly, as is described herein. The remaining therapy time is calculated at step 108, which also accounts for the fill percentage and/or remaining agent amount calculated at step 105. The remaining therapy time is based on a rate of consumption calculation for the particular anesthetic agent. For example, the approximate hourly consumption of Isoflurane, Halothane, and Enflurane anesthetic agents can be determined as 3*VC*FGF, where VC is the vaporizer concentration and FGF is the fresh gas flow rate. For Sevoflurane, the approximate hourly consumption of anesthetic agent can be determined as 3.3*VC*FGF, where VC is the vaporizer concentration and FGF is the fresh gas flow rate. Other factors are also accounted for in the therapy time calculation, such as ambient pressure and temperature, carrier gas composition, etc.

Figure 8:
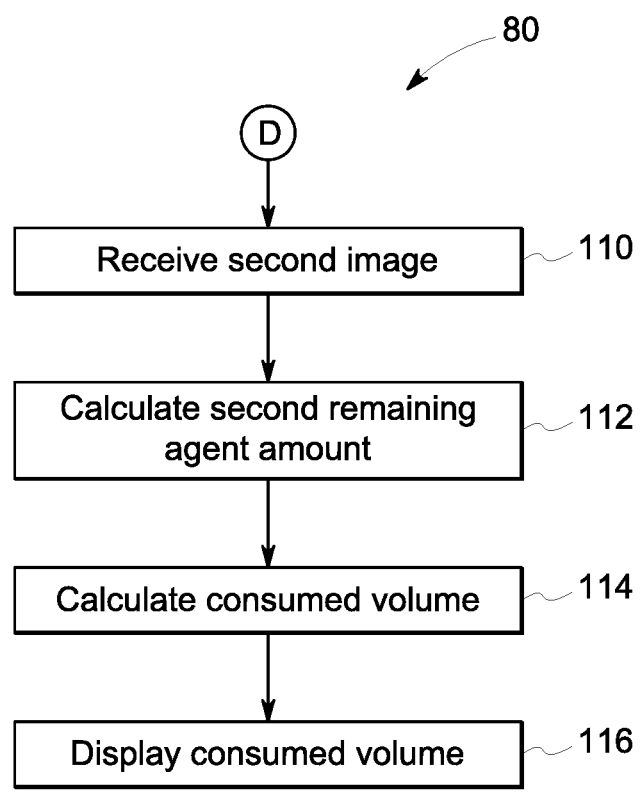

FIG. 8 depicts additional steps which may be calculated in certain embodiments of the agent level module 14 where the consumed volume 70 is calculated and tracked. A second image is received at step 110 and a second remaining agent amount is calculated at step 112, according to the methods described above. A consumed volume is then calculated at step 114 by determining a difference between a first remaining agent amount and the second remaining agent amount. The consumed volume is then displayed at step 116, such as on the user interface display 18 associated with the system 10. For example, the consumed volume 70 may be provided in the agent information image 45 containing the second remaining agent amount and other information determined based on the second image.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for monitoring anesthetic agent fill level in vaporizer reservoir, the system comprising:
   a camera configured to capture an image containing a sight glass on the vaporizer reservoir;
   a display;
   a processor;
   an agent level module executable on the processor to:
      locate a sight glass portion within the image;
      locate an agent level edge within the sight glass portion of the image;
      locate a minimum reference point and a maximum reference point within the image;
      calculate fill percentage based on a position of the agent level edge relative to the minimum reference point and the maximum reference point;

access a known volume of the vaporizer reservoir;
calculate a remaining agent information based on the fill percentage and the known volume of the vaporizer reservoir; and
display the remaining agent information on the display.

2. The system of claim 1, wherein the agent level module is further executable to:
locate an agent label within the image; and
identify anesthetic agent type in the vaporizer reservoir based on visual recognition of the agent label.

3. The system of claim 2, wherein the agent level module is further executable to:
receive a fresh gas flow rate;
receive a vaporizer concentration;
wherein the remaining agent information includes a remaining agent amount based on the fill percentage and the known volume of the vaporizer reservoir and a remaining therapy time calculated based on the fresh gas flow rate, the vaporizer concentration, and the remaining agent amount.

4. The system of claim 3, wherein the agent level module is configured to generate a prompt on the display for an operator to enter the fresh gas flow rate and the vaporizer concentration.

5. The system of claim 2, wherein the agent level module is further configured to:
detect one of a standard color indicator for anesthetic agent type as the agent label; and
determine the anesthetic agent type in the vaporizer reservoir based on the detected standard color.

6. The system of claim 1, wherein the agent level module is further configured to:
calculate a first remaining agent amount based on a first image containing a sight glass, and calculate a second remaining agent amount based on a second image containing the sight glass;
calculate a consumed volume based on a difference between the first remaining agent amount and a second remaining agent amount; and
display the consumed volume on the display.

7. The system of claim 6, wherein the agent level module is further configured to store the first image, the second image, and the consumed volume in a patient medical record.

8. The system of claim 1, wherein the agent level module is further configured to receive a vaporizer system identifier, and to access a lookup table containing known volumes based on the vaporizer system identifier.

9. The system of claim 8, wherein the agent level module is further configured to:
locate a fill port within the image;
locate an agent label with respect to the fill port; and
determine the vaporizer system identifier based on the location of the agent label with respect to the fill port.

10. The system of claim 1, wherein the minimum reference point is a lower edge of the sight glass within the image and the maximum reference point is an upper edge of the sight glass within the image.

11. A method for monitoring anesthetic agent fill level in a vaporizer reservoir, the method comprising:
receiving an image of the vaporizer reservoir, the vaporizer reservoir having a known volume for containing liquid anesthetic agent;
using machine vision software;
locating a sight glass portion within the image;
locating a minimum reference point and a maximum reference point within the image;
locating an agent level edge within the sight glass portion of the image;
calculating a fill percentage based on a position of the agent level edge relative to the minimum reference point and the maximum reference point;
calculating a remaining agent information based on the fill percentage; and
display the remaining agent information.

12. The method of claim 11, further comprising locating an agent label within the image, and determining an anesthetic agent type in the vaporizer reservoir based on the agent label.

13. The method of claim 12, further comprising:
detecting one of a standard color indicator for anesthetic agent type within the image of the agent label; and
determining the anesthetic agent type in the vaporizer reservoir based on the detected standard color.

14. The method of claim 12, further comprising:
locating a fill port within the image;
locating the agent label with respect to the fill port; and
determining a vaporizer system identifier based on the location of the agent label with respect to the fill port.

15. The method of claim 11, further comprising:
receiving a vaporizer system identifier;
accessing a lookup table containing known volumes based on the vaporizer system identifier;
calculating a remaining agent amount based on the known volume and the fill percentage.

16. The method of claim 15, further comprising:
receiving a fresh gas flow rate and a vaporizer concentration;
calculating a remaining therapy time based on the fresh gas flow, the vaporizer concentration, an anesthetic agent type, and the remaining agent amount.

17. The method of claim 16, wherein displaying the remaining agent information includes generating an overlay display of at least one of the remaining agent amount and the remaining therapy time, and providing the overlay display on the image containing the sight glass.

18. The method of claim 17, wherein the minimum reference point is a minimum fill line marking on or adjacent to the sight glass and the maximum reference point is a maximum fill line marking on or adjacent to the sight glass, and wherein the overlay display includes at least one of a minimum fill line indicator overlaid on the image at the located minimum reference point and a maximum fill line indicator overlaid on the image at the located maximum reference point.

19. The method of claim 16, further comprising communicating with a vaporizer control system to receive the fresh gas flow rate and the vaporizer concentration.

20. The method of claim 11, wherein the remaining agent information includes a first remaining agent amount, and further comprising:
calculating a second remaining agent amount based on a second image of the vaporizer reservoir;
calculating a consumed volume based on a difference between the first remaining agent amount and a second remaining agent amount; and
displaying the consumed volume on the display.

* * * * *